United States Patent [19]

Fishel et al.

[11] Patent Number: 5,522,974

[45] Date of Patent: Jun. 4, 1996

[54] METHOD OF PREPARING GEL CONTAINING CAPILLARIES

[75] Inventors: Laurence A. Fishel, 1224 E. Saginaw St., #18, East Lansing, Mich. 48823; Barnett Rosenberg, Holt; David A. Juckett, East Lansing, both of Mich.

[73] Assignee: Laurence A. Fishel, East Lansing, Mich.

[21] Appl. No.: 140,680

[22] Filed: Oct. 21, 1993

[51] Int. Cl.$^6$ ........................................... C08L 5/00
[52] U.S. Cl. ........................... 264/104; 204/455; 204/605; 524/56; 524/57; 524/58
[58] Field of Search ............................ 204/182.8, 299 R; 524/56, 57, 58

[56] References Cited

U.S. PATENT DOCUMENTS

| | | | |
|---|---|---|---|
| 4,810,183 | 3/1989 | Place et al. | 425/434 |
| 4,854,706 | 9/1989 | Karger et al. | 204/182.8 |
| 4,874,491 | 10/1989 | Stålberg | 205/182.8 |
| 4,883,597 | 11/1989 | Perlman | 210/640 |
| 4,897,306 | 1/1990 | Sugimoto et al. | 428/336 |
| 4,948,480 | 8/1990 | Christy, Jr. et al. | 204/182.8 |
| 4,997,537 | 3/1991 | Karger et al. | 204/182.8 |
| 5,061,355 | 10/1991 | Rose, Jr. | 204/182.8 |
| 5,064,769 | 11/1991 | Gambert et al. | 436/516 |
| 5,066,376 | 11/1991 | Osterhoudt et al. | 204/182.8 |
| 5,085,756 | 2/1992 | Swedberg | 204/299 |
| 5,110,439 | 5/1992 | Holloway | 204/299 |
| 5,112,460 | 5/1992 | Karger et al. | 204/182.8 |
| 5,141,612 | 8/1992 | Schomburg et al. | 204/182.8 |
| 5,159,049 | 10/1992 | Allen | 524/56 |
| 5,190,629 | 3/1993 | Sugihara et al. | 204/182.8 |
| 5,228,971 | 7/1993 | Brumley, Jr. et al. | 204/299 R |

FOREIGN PATENT DOCUMENTS

| | | |
|---|---|---|
| 0272925 | 6/1988 | European Pat. Off. . |
| WO92/00795 | 1/1992 | WIPO . |

OTHER PUBLICATIONS

"Preparation of Polyacrylamide Gel–Filled Capillaries for Capillary Electrophoresis", by Dolnik et al., published in *J. Microcol. Sep.*, Sep. 3, 1991, vol. 3, pp. 155–159.

*Primary Examiner*—Arun S. Phasge
*Attorney, Agent, or Firm*—Gifford, Krass, Groh, Sprinkle, Patmore, Anderson & Citkowski

[57] ABSTRACT

Described is a method of preparing polyacrylamide gel containing capillary tube wherein acrylamide is polymerized from a liquid to a gel within the tube, the improvement comprising the steps of: a) after the polymerization, annealing the gel inside the tube by cycling the gel/tube at least once in a temperature range from 20° C. to a temperature not to exceed about 75° C. and back to ambient; and b) recovering the stress released gel-filled tube. Preferably, the polymerization commences at the middle of the tube and commences toward the extremities of the tube.

12 Claims, No Drawings

5,522,974

METHOD OF PREPARING GEL CONTAINING CAPILLARIES

TECHNICAL FIELD

The present invention is concerned with preparing polyacrylamide gel containing capillary tubes wherein the acrylamide is polymerized from a liquid to a gel within the glass tube.

BACKGROUND OF THE INVENTION

Acrylamide polymers are used in a wide variety of chromatographic and electrophoretic techniques and are used in capillary electrophoresis. Polyacrylamide is well suited for size fractionation of charged macro molecules such as proteins, polydeoxyribonucleic acids (DNA) and polyribonucleic acids (RNA) and when used as the matrix inside narrow bore capillaries, should greatly increase the sensitivity, efficiency, speed and resolution of electrophoretic separation and analysis of such molecules in complex mixtures.

U.S. Pat. No. 5,112,460 describes high performance micro capillary gel electrophoresis, hereby incorporated by reference. The patent indicates extremely high resolution separations of materials having different effective charges have been achieved by open tubular free-zone electrophoresis and isotachophoresis in narrow capillary tubes. In addition, bulk flow can be driven by electro osmosis to yield very sharp peaks. The patent is primarily directed toward preparing a coating material that is covalently bonded to the inner surface of the microcapillary tube prior to the preparation of the polymeric gel.

In a similar fashion, see U.S. Pat. Nos. 5,110,439 and 5,085,756, both hereby incorporated by reference.

Other references address the issue of preventing shrinkage defects during and after polymerization such as European Patent Application 272,925, published Jun. 29, 1988. Other references which are concerned with polyacrylamide gel electrophoresis are as follows: U.S. Pat. Nos. 5,141,612; 5,061,355; 5,064,769; 5,066,376; 4,997,537; 4,948,480; 4,897,306; 4,883,597; 4,874,491; 4,865,706; PCT Publication No. WO92/00795, published Jan. 23, 1992; and a paper entitled "Preparation of Polyacrylamide Gel Filled Capillaries For Capillary Electrophoresis," by Dolnik et al, published in JOURNAL OF MICROCOLUMN SEPARATIONS, Sep. 3, 1991, Vol. 3, pp. 155–159.

None of the references suggest an annealing technique of the present invention wherein subsequent to polymerization, the gel-filled capillary is cycled to an increased temperature and then cooled once and preferably several times. It is an object of the annealing technique to maintain void free gels within the capillarly tube. It is an object of the present invention to maintain the gel-filled capillaries void free particularly after the imposition of voltage during an electrophoresis separation.

The annealing makes the gel more resilient and increases its resistance to void formation during temperature changes (e.g. storage in a refrigerator) or from physical stresses, (e.g. breaking or cutting the end of capillary/gel). The annealing feature releases the stresses in the formation of the polymer.

SUMMARY OF THE INVENTION

Described is a method of preparing a poly-acrylamide gel containing capillary tube wherein acrylamide is polymerized from a liquid to a gel within the tube, the improvement comprising the steps of, after the polymerization, annealing the gel inside the tube by cycling the gel/tube at least once in a temperature range from about 20° C. to a temperature not to exceed about 75° C. and back to ambient; and recovering the stress released gel filled tube.

DESCRIPTION OF PREFERRED EMBODIMENTS

As polyacrylamide is formed during the polymerization of a mixture of acrylamide and a cross-linker, N,N'-methylenebisacrylamide, the gel contracts. If the rate and direction of the polymerization reaction in a capillary tube are not properly controlled, this contraction results in the formation of voids in the polyacrylamide gel, often equal in diameter to the internal diameter of the capillary tube itself. In the case of the much larger slabs or tube polyacrylamide gels currently used in many laboratories, the presence of voids of this size is of little consequence. However, in narrow-bore capillaries, such voids represent a very serious problem.

A new procedure for preparing void-free polyacrylamide gels inside fused silica capillary tubing is described here. Polymerization of the acrylamide/NN'-methylenebisacrylamide gel solution is directed to occur beginning at the midpoint of the capillary tube, and thereafter proceeding outward toward each end. Thus, as the polymerization reaction occurs on either side of the initial site and the gel contracts, the entire column of unreacted solution distal to that site is pulled towards the midpoint. When the entire solution has polymerized inside the full length of the capillary tube, a space remains at both ends. Preparation of void-free polyacrylamide gel-containing capillary tubing depends on the reaction mixture composition and the reaction rate.

To control both the direction and the rate of acrylamide polymerization in the capillary tube, an insulated apparatus has been developed that is rectangular in shape and about four inches in depth. It consists of two cooling tubes inside of which is held the capillary that has been filled with the acrylamide mixture. The cooling tubes are motor-driven along a track in opposite directions at a controllable rate. As the cooling tubes slowly move apart, the capillary tube is exposed and thus warmed to room temperature from the midpoint outward towards the two ends. The ratio of the rate at which the gel solution polymerizes at room temperature (about 25° C.) and its rate in the cooling tubes is important in determining the length of void-free capillary tube that can be prepared.

Gel-filled capillaries can be prepared from an alternative apparatus which consists of two brass plates to the bottom or underside of which was soldered copper tubing in a zig-zag fashion. Coolant, whether it be warm or cold water (or water-ethylene glycol mixtures), is pumped to control the plate temperature. One plate may be maintained at near 0° C. while the other maintained at a higher temperature, for example, 28.5° C. On top of each plate is a rectangular glass plate which is positioned above the brass plate on plastic strips placed at the end of each of the glass plates that had been greased with a high vacuum silicon grease to form an effective barrier or seal against water. The two brass plates, and therefore the two glass plates resting on them, were separated by a narrow gap (about 3 millimeters). Each elevated glass plate was a cover or lid for water, that is, between the brass plate and the glass plate, the entire space was filled with water. This was allowed to equilibrate to the temperature of the brass plate before beginning polymerization of a gel. Capillary action kept the water from running out from beneath the glass plates. Additionally, high vacuum silicon grease was also applied around the edges of the glass plate and the surface of the brass plate immediately beneath the glass at the exposed edges of the glass in order to better contain the water beneath the glass plate. The distance of the glass plate above the brass plate was generally about 3 millimeters.

To pull a capillary in its holder along the plate, a syringe pump functions as the drive unit. The rate at which the capillary was pulled is something that may be determined empirically, but this varied depending upon the type of gel and concentration of the monomer/cross-linker used. The higher the percentage (%T), the slower the rate of travel required. The temperature also may be optimized for each type of capillary gel. One may adjust the %T (total percentage of acrylamide monomer+cross-linker) and the %C (cross-linker percentage) as desired.

Insulation such as styrofoam may also be used to better maintain the temperatures of the plates and thus the capillary and polymerizing gel solution within.

The capillary temperature and the polymerization of the gel can best be accomplished by automated, computer-controlled equipment that correctly maintains and then varies at the desired rate, the temperature along the capillary. In other words, the tube could be maintained at one location and the temperature along the tube starting from the middle and out toward the extremities thereof could be varied to give a desired polymerization rate as well as an annealing rate. Most desirably, the annealing rate is at 1 degree Centigrade (1° C.) per minute or less. Obviously, the rate may be slower but it is a function of a desired production rate of gel-filled capillaries.

The most desired polymerization and annealing steps would be to polymerize the acrylamide materials and then allow them to be stabilized by allowing them to sit for several hours. Immediately thereafter, the temperature of the capillary would be raised to a maximum of 75° C. and then slowly cooled. The temperature cycle can be a maximum of 55° C. as desired. Alternatively, the temperature could be decreased to 20° C. and then raised to the desired upper limit. This cycle could occur several times as desired depending on the polymeric materials and the capillary size.

The computer-controlled instrument is preferably one utilizing thermoelectric modules (Peltier effect).

The microcapillary may be made of any variety of materials provided the gel system to be employed and the electrophoresis technique can function adequately with the particular materials employed. Suitable materials include glass, alumina, beryllia, and Teflon® (trademark of DuPont for fluoropolymers) coated materials. Preferably, the microcapillary is made of fused silica.

The microcapillary dimensions are important because, for a given electric field, as the internal diameter of the microcapillary is reduced, the electric current and the resultant heating produced by a particular applied electric field is reduced. Thus, for highest resolution separations, it is desirable that the microcapillary have a minimum internal diameter. With the improved microcapillaries of this invention, however, this factor is somewhat less important than formerly. Accordingly, microcapillaries having internal diameters in the range between 5 and 2000 micrometers function in the invention. A preferred range of internal diameters is 10 to 200 micrometers. A polyimide coating on the outer surface of the microcapillary permits easy handling of thin-walled microcapillaries.

It is believed therefore that voids or bubbles in the gel-filled capillaries of this invention are not formed after the imposition of current during an electrophoresis separation.

The polymeric gel material to employ can be any polymer which has a pore structure which can be varied. It may or may not be a cross-linked polymer whose pore structure is varied by varying the amounts of monomer and cross-linking agent, and the reaction conditions. Examples of suitable polymeric systems are polyacrylamide, agarose, and mixtures of agarose and polyacrylamide. A preferred polymeric gel material is based on acrylamide and NN'-methylenebisacrylamide, the N,N'-methylenebisacrylamide serving as a cross-linking agent. Other possible cross-linking agents are N,N'-(1,2-dihydroxyethylene)-bisacrylamide, N,N'-diallyltartardiamide, and N,N'-cystamine-bisacrylamide. Still other monomers and cross-linkers will suggest themselves to those skilled in the art.

The polymerization reaction is preferably initiated with ammonium persulfate or N,N,N',N'-tetramethyleneethylenediamine, though other free radical polymerization initiators may be employed, as known by those skilled in the art.

The layer between the polymeric gel and the inner surface of the microcapillary wall is generally a hydrophobic material and is derived from a coating reagent which is capable of chemically bonding to the microcapillary wall. The reagent is generally a molecular chain having an appropriate reactive functional group at one end, though non-chain type molecules having appropriate functionalities will also serve. The end of the coating reagent which is to bond to the capillary wall carries a reactive functional group which can bond chemically to silanol groups or other reactive functionalities on the inner surface of the microcapillary. Such reactive functional groups of the reagent are typically reactive silanes such as trialkoxysilane, trichlorosilane, mono, di, or tri-enolate silanes, and aminosilanes, where the silicon atom carries at least one group which may be readily displaced. Examples of suitable coating reagents are materials such as alkyl di- or tri-ethoxy or methoxy silanes, and alkylether di- or tri-ethoxy or methoxy silanes.

In a preferred embodiment, the coating reagent is a bifunctional material, which also contains a second functional group capable in principle of forming a covalent bond with the polymeric gel material. Such functional groups include vinyl, substituted vinyl, or any group which upon cleavage yields a free radical, but for practical purposes a vinyl group is preferred because it is then possible to form the polymeric gel in the microcapillary and chemically bond it to the microcapillary wall simultaneously. Representative bifunctional reagents are 3-methacryloxypropyl-trimethyoxysilane, and 3-methacryloxypropyldimethylethoxysilane, shown as a) and b) below:

a) 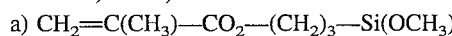
CH$_2$=C(CH$_3$)—CO$_2$—(CH$_2$)$_3$—Si(OCH$_3$)$_3$ b) 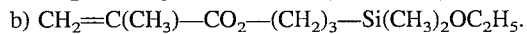
CH$_2$=C(CH$_3$)—CO$_2$—(CH$_2$)$_3$—Si(CH$_3$)$_2$OC$_2$H$_5$.

Other possible bifunctional reagents are vinyltriacetoxysilane, vinyltri(-methoxyethoxy) silane, vinyltrichlorosilane, and methylvinyldichlorosilane, this list being intended as illustrative but not exhaustive.

The silane material may be applied to the inner surface of the glass tube by first washing the tube with water and drying it in the presence of nitrogen. The silane, with or without solvent such as ethanol, is then applied directly to the interior of the tube. The silane is then dried in the presence of nitrogen. Thereafter, the polymerizable materials may be inserted into the tube as described herein.

Known cross-linking agents can be employed singly or in combination in the preparation of the aqueous gel layer.

Examples of the cross-linking agents include bifunctional compounds such as N,N'-methylenebisacrylamide (BIS), N,N'-propylenebisacrylamide (PBA); di (acrylamidodimethyl) ether (DAE), 1,2-diacrylamide ethyleneglycol (DEG), ethyleneureabisacrylamide (EDA), N,N'-diallyltartardiamide (DATD) and N,N'-biasacrylylcystamine (BAC), and trifunctional compounds such as triallylcyanurate, triallylisocyanurate, 1,3,5-triacryloylhexahydro-s-triazine. The cross-linking agents are described, for instance, in "Electrophoresis" 1981, 2, 213–228.

If urea is utilized as a component of the gel-forming composition, it is desirable to add acetamide to prevent crystallizing thereof. Preferably, if urea is utilized, it is utilized in the amount of approximately 6.95 molar with 0.05 molar acetamide.

When the glass tube is fused silica, an organosiloxane solution is utilized to bind the gel to the glass. That may be a silanol terminated polydimethylsiloxyane. The vinyl coupling reagent can include methyacryloxypropyltrichlorosilane. The cross-linking agent is the monomer as described above. Sometimes a buffer such as SDS-PAGE (sodium dodecyl sulfate polyacrylamide gel electrophoresis) buffer such as TRIS-HCl is utilized and the resulting structured the gel matrix, is bound to the tube via the tether layer. Each tether is a silane terminated polyorgano siloxane polymer segment.

After the gel is formed within the fused silica, it goes through an annealing process. By this is meant that the gel-filled tube is cycled to a desired temperature and then the temperature reduced to ambient. The purpose of the annealing is to reduce the voids that may form during subsequent handling of gel-filled tubes. The maximum annealing temperature would be 75° C., preferably less than 50° C., and even more preferably no greater than about 45° C.

Most preferably, the gel-filled tube is placed into a sealed plastic bag which contains a TRIS-borate buffer that is used during the polymerization process. The bag is immersed in a constant temperature bath and the temperature raised and decreased as desired. Preferably, the maximum temperature that is reached is maintained for a period of time of about 10 minutes to 1 hour, preferably approximately 10–20 minutes, and even more preferably about 15 minutes. An indication that the gel-filled tube would be void-free is to be able to store the gel-filled tube after the annealing process in a refrigerator at about 1–3° C. In addition, another technique for determining a void-free gel-filled tube is obtained is that the tube could be cut without void formation. In essence, the annealing process reduces the stress that is formed during the polymerization process.

While applicant does not wish to be bound to any theory, it is believed that the annealing step allows the polymer to be as linear as possible to relieve stresses formed during polymerization. The annealing allows the released polymer to handle ion flow better and to handle temperature changes better.

Alternatively, the gel-filled tube could be heated or cooled using Peltier junctions and therefore no need to move the tubes. Also, from a quality control perspective, the completed tubes may be examined with a microscope (100× power) to determine the absence of voids.

Listed below are descriptions of preferred embodiments wherein all temperatures are in degrees Centigrade and all parts are parts by weight, unless otherwise indicated.

EXAMPLE 1

The following procedure has been successfully used to produce void-free polyacrylamide gels in 75 µm inner diameter fused silica tubing in lengths up to and including 1.24 meters. It is expected that longer lengths are possible. Acrylamide; N,N'-methylenebisacrylamide ("bis"); ammonium persulfate (AP) and N,N,N',N'-tetramethylethylenediamine (TEMED) were purchased from BDH Limited (Electran).

Tris(hydroxymethyl)aminomethane ("TRIS") and boric acid were of reagent grade. Solutions of acrylamide/bis/TRIS-borate and AP prepared in distilled, deionized H$_2$O were filtered (0.22 µm) before use. Only glass containers were used. The final concentrations of reagents in the acrylamide gel mixture were: 7.2% (w/v) acrylamide; 0.25% (w/v) bis; and 0.1mM Tris/0.1mM borate (from pH 8.3 stock).

The inside of each capillary tube was first coated with γ-methacryloxypropyltrimethoxysilane to covalently link the polyacrylamide to the glass surface. 2 ml of the acrylamide gel mixture were de-gassed at about 25° C. for 60 minutes in a glass test tube. After de-gassing, the tube was covered tightly with Parafilm and placed in a +1.3° C. cooling bath for 9 minutes. The internal temperature of the cooling tubes was about +2.0° C. While the gel mixture was cooling, the capillary tube was inserted into the cooling tubes. At 9 minutes, the cooled gel mixture was placed on ice, and 7.5 µl of 10% AP and 3.0 µl of TEMED were added. A P-1000 Pipetman (Gilson) set at 1.0 ml was used to mix the solution on ice by gently pipetting it up/down 10 times, trying not to introduce any air bubbles. The solution was then drawn into the capillary tube by suction using a 5 ml syringe attached to the opposite end of the capillary. The entire mixing and filling procedure was completed in about 7 minutes. The syringe was then removed and the cooling tubes driven apart to create a 1 cm gap, thus exposing 1 cm around the midpoint of the capillary tube. The drive was then stopped and this 1 cm length of capillary allowed to remain at room temperature (about 25° C.) for 10 minutes, to cause the acrylamide to polymerize in this region. At 10 minutes, a clip was attached at the midpoint of the capillary to hold the capillary stationary, and the cooling tubes driven at the rate of 1 cm/minute away from the midpoint.

Of great importance is the difference in the rate of polymerization of the acrylamide gel mixture at room temperature (about 25° C.) and at +2.0° C. That is, the mixture polymerizes at a much faster rate at the warmer temperature. In the example cited above, the gel mixture was about 50% polymerized 83 minutes after the TEMED was added to initiate the reaction. The actual rate inside the capillary tube at room temperature has not been accurately measured, but it appears to reach completion in about 3–4 minutes. Two sources of variability in polymerization rate are the concentrations of AP and TEMED, which were pipetted using a P-20 Pipetman, and oxygen introduced into the final acrylamide solution when these two reagents were mixed in by repeated pipetting with a P-1000 Pipetman—oxygen being a potent inhibitor of the polymerization reaction. Both problems are easily soluble; particularly so in an automated system where all procedures can be carried out under anaerobic conditions.

After polymerization of the acrylamide inside a narrow-bore capillary tube, it is necessary to anneal the gel to release strain created during the polymerization reaction. Otherwise storage of the capillary at reduced temperatures (such as in a refrigerator) or attempting to cut the capillary/gel will result in void formation. The following procedure for strain release was developed. The gel-filled capillary tube was sealed inside a plastic bag filled with the same tris-borate buffer used in the polymerization reaction, and the bag was immersed in a constant temperature bath maintained at 25° C. The bath temperature was then gradually raised to 40° C., where it was kept for 15 minutes. The temperature was then gradually lowered back to 25° C., and the cycle repeated once more. The gel now had these properties and it could be stored in a refrigerator at +1.5° C. and the capillary tubing/ gel could be cut to any length, both without void formation.

A variation of the method described above involves the use of a photoactivatible molecule such as riboflavin 5'-phosphate to permit control of the rate and direction of polymerization by irradiation of the gel solution in the capillary tube with ultraviolet light. Preliminary experiments with photopolymerization of the polyacrylamide gel showed the utility of this method for preparing void-free gels in narrow-bore capillaries. However, due to the nature of the chemical reactions occurring during polymerization of the gel solution, a small percentage of the photocatalyst molecule (e.g. riboflavin 5'-phosphate) may become tightly bound into the polymerized gel and may not be removed. This has a tendency to cause a high background fluorescence when the gel is irradiated with ultraviolet light. Thus, such gels would be unsuitable for use in an analytical system based on fluorescence (depending on wave length utilized), but would be useful when other methods such a voltammetric detection are employed. Using a photoinitiator that does not fluoresce would avoid this problem.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting, and that various changes may be made without departing from the scope or spirit of the invention.

What is claimed is:

1. In a method of preparing a gel containing capillary tube wherein a material is polymerized from a liquid to a gel within the tube, the improvement comprising the steps of:
   a) after the polymerization, annealing the gel inside the tube by thermally cycling the gel/tube at least once, under conditions which will not shrink or dry the gel, from a first temperature to a second temperature which is greater than said first temperature, so as to release stress in said gel; and
   b) recovering the stress released gel-filled tube.

2. The method of claim 1 wherein the annealing cycle includes heating the polymerized gel/tube at a rate of about 1° C./minute.

3. The method of claim 1 wherein the second temperature is about 55° C.

4. The method of claim 1 wherein the tube is glass.

5. A method as in claim 1 wherein the step of annealing comprises thermally cycling said gel/tube at least twice.

6. The product of the process of claim 1.

7. A method of preparing a void-free gel-filled tube comprising the steps of:
   a) filling the tube with a polymerizable liquid;
   b) adjusting the temperature of the filled tube to lower than 10° C.
   c) commencing the polymerization at about the middle of the tube;
   d) continuing the polymerization toward the extremities of the tube;
   e) after the polymerization, annealing the gel inside the tube by thermally cycling the gel/tube at least once, under conditions which will not shrink or dry the gel, from a first temperature to a second temperature which is greater than said first temperature, so as to release stress in said gel; and
   f) recovering the stress released gel-filled tube.

8. The method of claim 1 wherein the annealing cycle includes heating the polymerized gel/tube at a rate of not greater than about 1° C./minute.

9. The method of claim 1 wherein the second temperature is about 55° C.

10. The method of claim 7 wherein the tube is glass.

11. A method as in claim 7, wherein the step of annealing comprises thermally cycling said gel/tube at least twice.

12. The product of the process of claim 7.

* * * * *

UNITED STATES PATENT AND TRADEMARK OFFICE
CERTIFICATE OF CORRECTION

PATENT NO.   : 5,522,974
DATED        : June 4, 1996
INVENTOR(S)  : Laurence A. Fishel, Barnett Rosenberg and David A. Juckett It is certified that error appears in the above-indentified patent and that said Letters Patent is hereby corrected as shown below:

Column 4, line 12: Replace "NN'" with --N,N'--.

Column 8, line 31: Replace "claim 1" with --claim 7--.

Column 8, line 34: Replace "claim 1" with --claim 7--.

Signed and Sealed this

Twenty-fifth Day of March, 1997

Attest:

BRUCE LEHMAN

Attesting Officer

Commissioner of Patents and Trademarks